(12) United States Patent
Feliz Matos et al.

(10) Patent No.: US 10,987,197 B2
(45) Date of Patent: Apr. 27, 2021

(54) INTRARADICULAR ANCHOR PIN

(71) Applicants: UNIVERSIDAD IBEROAMERICANA, UNIBE, Santo Domingo (DO); Leandro Edgardo Feliz Matos, Santo Domingo (DO); Elvin Alberto Mancebo Pacheco, Santo Domingo (DO); Dulce Concepcion Pereyra Guerrero, Santo Domingo (DO)

(72) Inventors: Leandro Edgardo Feliz Matos, Santo Domingo (DO); Elvin Alberto Mancebo Pacheco, Santo Domingo (DO); Dulce Concepcion Pereyra Guerrero, Santo Domingo (DO)

(73) Assignee: UNIVERSIDAD IBEROAMERICANA, UNIBE, Santo Domingo (DO)

( * ) Notice: Subject to any disclaimer, the term of this patent is extended or adjusted under 35 U.S.C. 154(b) by 0 days.

(21) Appl. No.: 15/773,245

(22) PCT Filed: Nov. 2, 2016

(86) PCT No.: PCT/DO2016/000003
§ 371 (c)(1),
(2) Date: May 3, 2018

(87) PCT Pub. No.: WO2017/076417
PCT Pub. Date: May 11, 2017

(65) Prior Publication Data
US 2018/0318040 A1    Nov. 8, 2018

(30) Foreign Application Priority Data
Nov. 5, 2015  (DO) .................................. P2015-0272

(51) Int. Cl.
*A61C 5/35* (2017.01)
*A61C 13/30* (2006.01)
*A61L 31/12* (2006.01)

(52) U.S. Cl.
CPC ................ *A61C 5/35* (2017.02); *A61C 13/30* (2013.01); *A61L 31/128* (2013.01); *A61C 2201/005* (2013.01)

(58) Field of Classification Search
CPC .................................. A61C 5/35; A61C 13/30
See application file for complete search history.

(56) References Cited

U.S. PATENT DOCUMENTS 1,743,910 A * 1/1930 Boatner .................... A61C 5/70
                                                             433/225
3,675,329 A * 7/1972 Weissman ................ A61C 5/35
                                                             433/225

(Continued)

FOREIGN PATENT DOCUMENTS

CH      561 052         * 4/1975
EP      2392291 A1 * 12/2011 ............. A61C 13/30

*Primary Examiner* — Ralph A Lewis
(74) *Attorney, Agent, or Firm* — Hoglund & Pamias, PSC; Roberto J. Rios

(57) ABSTRACT

The invention relates to an odontological biomaterial called "ANCLA Post". The post is used as a reconstruction means in anterior and posterior teeth, the cylindrical, conical design of the extension and anchor-shaped design of the apical end allowing forces to be adequately distributed to prevent the fracturing of the tooth and to keep same repairable and usable for a long time. The post is characterized in that it is made of fiberglass, resin or polymer, and is white and radiopaque.

5 Claims, 3 Drawing Sheets

(56) References Cited

U.S. PATENT DOCUMENTS

| | | | | | |
|---|---|---|---|---|---|
| 4,276,027 | A | * | 6/1981 | Lustig | A61C 5/35 |
| | | | | | 433/225 |
| 4,571,187 | A | * | 2/1986 | Weissman | A61C 13/30 |
| | | | | | 433/221 |
| 4,729,736 | A | * | 3/1988 | Weissman | A61C 5/35 |
| | | | | | 433/221 |
| 4,934,936 | A | * | 6/1990 | Miller | A61C 13/30 |
| | | | | | 433/220 |
| 5,741,139 | A | * | 4/1998 | Sicurelli, Jr. | A61C 13/30 |
| | | | | | 433/220 |
| 5,788,497 | A | * | 8/1998 | Chalifoux | A61C 13/30 |
| | | | | | 433/220 |
| 5,919,044 | A | * | 7/1999 | Sicurelli, Jr. | A61C 13/30 |
| | | | | | 433/220 |
| 6,776,617 | B2 | * | 8/2004 | Lax | A61C 8/0075 |
| | | | | | 433/221 |
| 7,488,175 | B2 | * | 2/2009 | Karmaker | A61C 13/30 |
| | | | | | 433/220 |
| 8,197,256 | B2 | * | 6/2012 | Lu | A61C 13/30 |
| | | | | | 433/220 |
| D730,523 | S | * | 5/2015 | Sicurelli | D24/156 |
| 2005/0123881 | A1 | * | 6/2005 | Karmaker | A61C 13/30 |
| | | | | | 433/220 |
| 2013/0071814 | A1 | * | 3/2013 | Boehner | A61C 13/30 |
| | | | | | 433/220 |

* cited by examiner

INTRARADICULAR ANCHOR PIN

TECHNICAL FIELD OF THE INVENTION

The invention relates to an intraradicular pin for anterior and posterior teeth having the lower end in the form of an anchor, specifically to an odontological biomaterial for the rehabilitation of anterior and posterior teeth treated endodontically, after a wide lesion of dental caries and with coronary destruction, serving as an intraradicular anchoring element and for supporting restorations.

Prior Art

Existing pins (posts) can be categorized into two large groups, metallic pins that can be cast and prefabricated and non-metallic pins based on fiberglass embedded in polymers, having as disadvantages the high incidence of irreparable dental fractures associated with them.

Both groups have been well studied via in vitro and in vivo clinical tests, so that the indications and contraindications of each one have been established in the literature. U.S. Pat. No. 4,729,736 A to IPCO CORP (US) published on Aug. 3, 1988 describes a dental post to safely retain a dental restoration in a prepared tooth. The dental post is formed by an elongated cylindrical pin having a longitudinal axis and helical grooves around the periphery of the pin for retaining the pin with cement inside the tooth.

Patent application RU2556526 to ARUTJUNOV SERGEJ DARCHOEVICH [RU]+, published on Jul. 10, 2015, describes two components: pins and stumps. The "post" component is made of computerized grinding ceramics and has an incrustation that can be accurately fixed to the walls of a prepared root canal, and a supraradicular portion in the form of a trunk of a prepared tooth for the permanent dental structure with a circular step inclined at an angle of 135 degrees. A cylindrical opening for the core in the form of a standard fiberglass pin of typical standard sizes is formed within the post along its length. A diameter of the prepared root canal is equal to a diameter of the fiberglass pin.

U.S. Pat. D730,523 (S1), "Dental Post" to SICURELLI ROBERT [US], published on 26 May 2015, shows a design of a dental fixing.

DESCRIPTION OF THE INVENTION

The solution proposed by our invention refers to an odontological biomaterial, with the lower end in the form of an anchor. This is used as a reconstruction means in anterior and posterior teeth, its cylindrical and conical design in its extension and its anchor shape at the apical end allows to distribute the forces in a suitable way to avoid dental fracture and keep it repairable and enabled for a long time. It is characterized by being made of 30% fiberglass, 70% resin and polymer, with a maximum flexion force of 1600 MPa, maximum compression force of 2000 Newton, radiopacity of 180%, total lengths from end to end are: 5 mm, 7 mm, 9 mm, 11 mm, 15 mm, 17 mm, 19 mm, and 21 mm, the lengths of the lower end with the anchor shape are: 1 mm, 3 mm, 5 mm and 7 mm, and the anchor-shaped lower end having diameters of: 0.9 mm, 1.0 mm, 1.14 mm, 1.25 mm, 1.40 mm, and 1.50 mm. Elastic flexural modulus of 90 Gpa and two tones, translucent and white.

BRIEF DESCRIPTION OF THE DRAWINGS

The drawings presented are for illustrative purposes and do not limit the invention.

DETAILED DESCRIPTION OF THE INVENTION

Figure 1:
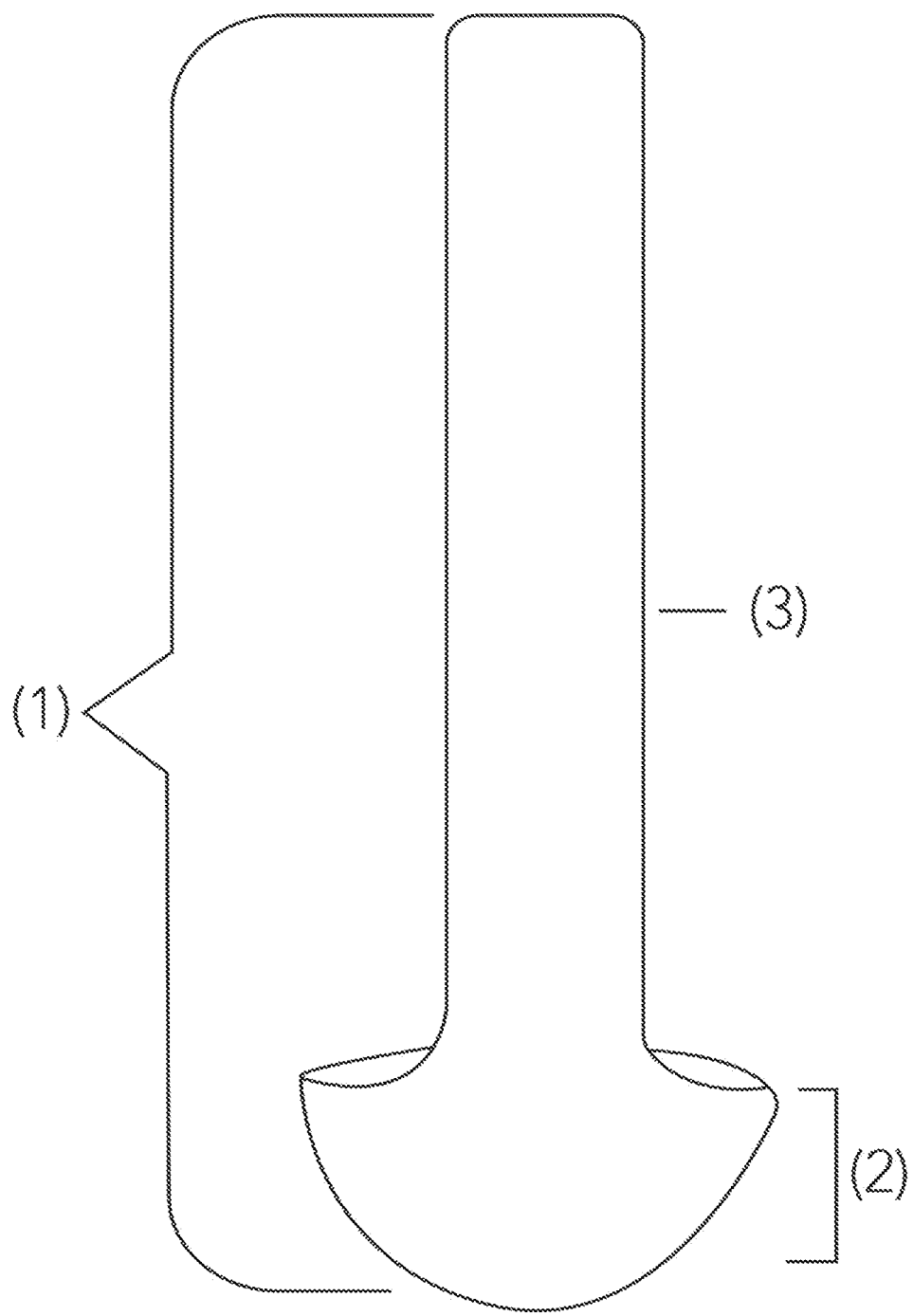
FIG. 1 represents the intraradicular pin with the lower end in the shape of an anchor.

The intrarradicular pin with the lower end in the form of an anchor for anterior and posterior teeth has an anchor design at the lower end (apical) that functions as an aesthetic prefabricated intraradicular retention device, which adapts to the apical end of the root canal once it has been unsealed, passively residing within to allow reconstructing the stump with resinous and fibrous materials to receive the final restoration, as shown in FIG. 1.

Figure 3:
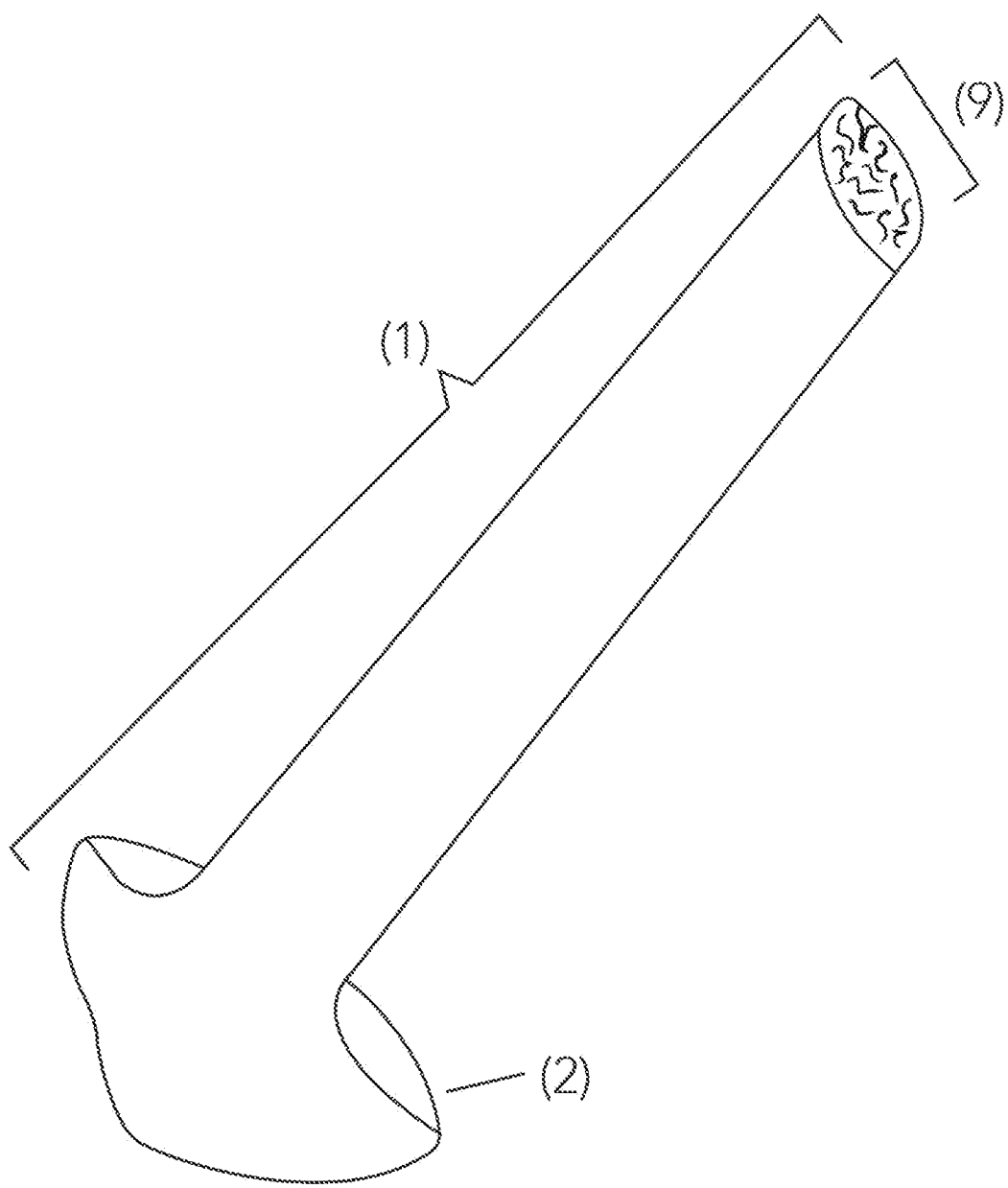
FIG. 3. Represents a perspective view of the intraradicular pin with the lower end in the form of an anchor.

The total lengths of the intarradicular pin with the lower end in the form of an anchor are: 5 mm, 7 mm, 9 mm, 11 mm, 15 mm, 17 mm, 19 mm, and 21 mm from end to end (FIG. 1, element 1), with apical anatomical shape being the anchor itself at the lower end according to the apical internal space of the dental root with lengths of: 1 mm, 3 mm, 5 mm and 7 mm and diameters of: 0.9 mm, 1.0 mm, 1.14 mm, 1.25 mm, 1.40 mm, and 1.50 mm as shown by element (2) in FIGS. 1 and 3.

An objective of the intraradicular pin with the lower end in the shape of an anchor is to allow the rehabilitation of all the dental organs (anterior and posterior teeth that need an intraradicular retention device to regain its main function of chewing as well as phonation, swallowing and aesthetic losses.

In addition, it also allows the passive reconstruction of the tooth, decreases the tension in the lateral walls, improves the intraradicular element retention and offers the possibility of performing an aesthetic dental reconstruction. The pin with the lower end in the form of an anchor requires little time for its installation in a tooth and is inexpensive.

The pin with the lower end in the shape of an anchor is designed to comply with the static and dynamic functions of dental chewing under its indications, inserting and reconstructing techniques, with a maximum flexion force of 1600 Mpa, supporting compression forces up to the 2000 newtons, and an elastic flexure modulus of 90 GPA as tested in the MTI 2 k universal assays system (USA). These characteristics allow that when there is a fracture in the pin with the lower end in the form of an anchor, said fracture being of the disinsertion type, and therefore the tooth can be repaired.

Figure 2:
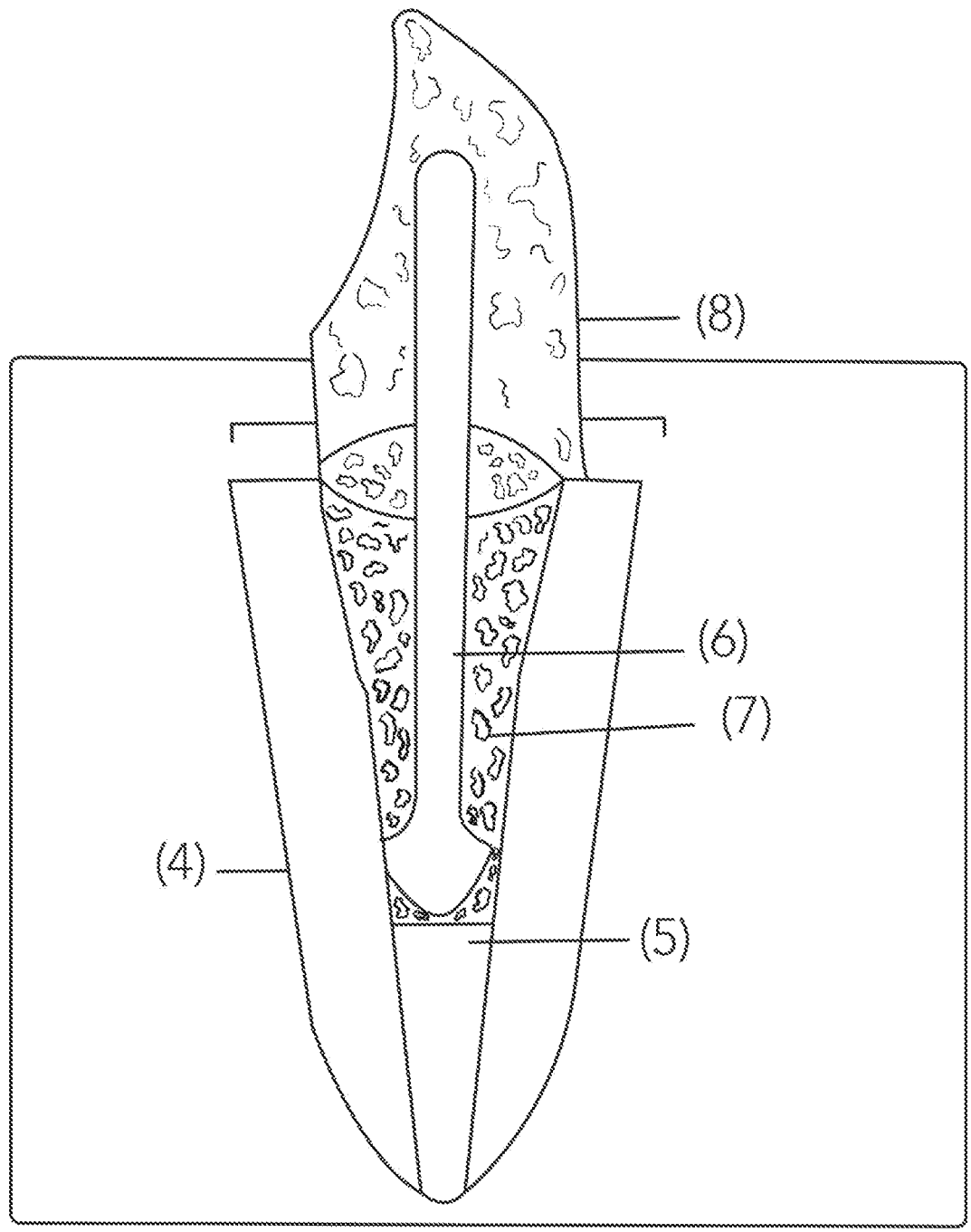
FIG. 2 represents the dental organ prepared after an endodontic treatment and with the intraradicular pin with the lower end in the form of an anchor inserted.

In order to use the pin with the lower end in the form of an anchor, a tooth root must be in good condition as illustrated by element (4) in FIG. 2, and with endodontic treatments already performed (ducts), as shown in FIG. 2. The material placed in the endodontics (gutta-percha) is removed leaving 5 mm of the apical seal or at the end of the root as indicated by element (5) in FIG. 2, the diameter and length of the pin with the lower end in the form of anchor to be used is selected according to the dimension of the root canal with the radiography.

It is rectified with the drill-bit of the pin with the lower end in the form of anchor to be used avoiding circular movements, the pin with the lower end in the form of an anchor is tested and adjusted in the intra-conduit as illustrated by element (6) in FIG. 2.

The duct is cleaned and further conditioning and placement of resinous cement (element (7) in FIG. 2) of any brand inside the duct is carried out according to the cement manufacturer's recommendations. The selected pin with the lower end in the form of an anchor of two tones, translucent or white, is manually inserted slowly and the cement is allowed to set, normally by means of heat generation with illumination. After the bonding and hardness of the cement is verified, the stump is reconstructed (upper part of the tooth that supports the restoration with resin composite or resinous cement of any brand as shown by element (8) in FIG. 2. Finally, the stump is carved or prepared and the tooth is ready to receive a restoration which is usually a porcelain crown.

The invention claimed is:

1. Intraradicular pin for anterior and posterior teeth consisting of:
 a single piece element having a cylindrical continuous elongated part and an apical anchor part, wherein an anchor top portion of said apical anchor part laterally extends away from a bottom portion of the cylindrical continuous elongated part, said apical anchor part having a top diameter greater than a diameter of said cylindrical continuous elongated part and which is longitudinally reduced from said anchor top portion until reaching an end of said apical anchor part having a curved anchor bottom portion that is an end of said single piece element, effectively improving retention of the intraradicular pin.

2. Intraradicular pin according to claim 1, characterized by having 30% of fiberglass and 70% of a combination of resin and polymers achieving a maximum flexion force of 1600 MPa, a maximum compression force of 2000 Newton and being radiopaque up to 180%.

3. Intraradicular pin according to claim 1, characterized by the length from said top portion to said anchor bottom portion being selected from 5 mm, 7 mm, 9 mm, 11 mm, 15 mm, 17 mm, 19 mm, and 21 mm, the length from said anchor top portion to said anchor bottom portion being selected from 1 mm, 3 mm, 5 mm and 7 mm, and said top diameter being selected from 0.9 mm, 1.0 mm, 1.14 mm, 1.25 mm, 1.40 mm, and 1.50 mm, to effectively avoid irreparable dental fracture and total restoration of the tooth.

4. Intraradicular pin according to claim 1, characterized by having an elastic flexural modulus of 90 GPA.

5. Intraradicular pin according to claim 1, characterized by being provided in two tones: translucid and white.

* * * * *